United States Patent [19]

Lee

[11] Patent Number: 5,437,872
[45] Date of Patent: Aug. 1, 1995

[54] PHARMACEUTICAL COMPOSITIONS AND A DEVICE FOR ADMINISTERING THE SAME

[75] Inventor: William H. Lee, Essex, England
[73] Assignee: Bioglan Laboratories Ltd., England
[21] Appl. No.: 834,556
[22] PCT Filed: Aug. 24, 1990
[86] PCT No.: PCT/GB90/01321
   § 371 Date: Feb. 12, 1992
   § 102(e) Date: Feb. 12, 1992
[87] PCT Pub. No.: WO91/02518
   PCT Pub. Date: Mar. 7, 1991

[30] Foreign Application Priority Data

Aug. 25, 1989 [GB] United Kingdom .................. 8919446
Aug. 25, 1989 [GB] United Kingdom .................. 8919447

[51] Int. Cl.$^6$ ............................................. A61K 9/26
[52] U.S. Cl. .......................................... 424/464; 424/435;
   424/468; 424/469; 424/484; 424/488; 514/781
[58] Field of Search ................ 424/435, 464, 468, 469,
   424/484, 488

[56] References Cited

U.S. PATENT DOCUMENTS

| | | | |
|---|---|---|---|
| 4,226,849 | 10/1980 | Schor | 424/869 |
| 4,725,440 | 2/1988 | Ridgway et al. | 514/252 |
| 4,863,737 | 9/1989 | Stanley et al. | 424/440 |

FOREIGN PATENT DOCUMENTS

| | | |
|---|---|---|
| 452221 | 3/1973 | Australia . |
| 20059/88 | 2/1989 | Australia . |
| 0100157 | 2/1984 | European Pat. Off. . |
| 0157695 | 10/1985 | European Pat. Off. . |
| 0306454 | 3/1989 | European Pat. Off. . |
| 2624739 | 6/1989 | France . |
| 1583801 | 2/1981 | United Kingdom . |
| 2061950 | 5/1981 | United Kingdom . |
| 2111386 | 7/1983 | United Kingdom . |
| 2117239 | 10/1983 | United Kingdom . |

OTHER PUBLICATIONS

D. Northey et al., "Microbial Surveillance in a Surgical Intensive Care Unit", *Surgery Gynecology & Obstetrics*, vol. 139, No. 3, Sep. 1974, pp. 321–325.
M. Shield et al., "Systematic Bacteriological Monitoring of Intensive Care Unit Patients: The Results of a Twelve Month Study", *Intensive Care Medicine*, vol. 5, pp. 171–181, 1979.
J. Thorp et al., "A Survey of Infection in an Intensive Care Unit", *Anaesthesia*, vol. 34, 1979, pp. 643–650.
R. Weinstein et al., "Strategies for Prevention and Control of Multiple Drug–Resistant Nosocomial Infection", *The American Journal of Medicine*, vol. 70, Feb. 1981, pp. 449–454.
C. Stoutenbeek et al., "Nosocomial Gram–Negative Pneumonia in Critically Ill Patients", *Intensive Care Medicine*, vol. 12, 1986, pp. 419–423.
C. Stoutenbeek et al., "The Effect of Oral Non–Absorbable Antibiotics on the Emergence of Resistant Bacteria in Patients in an Intensive Care Unit", *Journal of Antimicrobial Chemotherapy*, vol. 19, 1987, pp. 513–520.
H. Rose et al., "Colonization of Intensive Care Unit Patients With Gram–Negative Bacilli", *American Journal of Epidemiology*, vol. 101, No. 6, pp. 495–501. Jan./1975.
The Dow Chemical Company, "Formulating for Controlled Release with METHOCEL® Premium Cellulose Ethers", Oct. 1989.
Facts and Comparisons, Olin, Mouth and Throat Products, p. 521, May 1988.

*Primary Examiner*—Thurman K. Page
*Assistant Examiner*—James M. Spear
*Attorney, Agent, or Firm*—Oliff & Berridge

[57] ABSTRACT

A pharmaceutical tablet or lozenge is described, which comprises a non-absorbable pharmaceutically active agent, in combination with a tablet matrix, arranged for providing controlled and sustained release of said agent into the mouth and gastro-intestinal tract, from a buccal or sub-lingual location. Also disclosed, are buccal tablets formed from non-carigenic sugars and a device for holding a tablet or lozenge in a location within a patient's mouth, from which an active ingredient, from the tablet or lozenge, is releasable by the action of the patient's saliva.

31 Claims, 1 Drawing Sheet

PHARMACEUTICAL COMPOSITIONS AND A DEVICE FOR ADMINISTERING THE SAME

DESCRIPTION

The present invention relates to improved pharmaceutical compositions. In particular, the present invention relates to pharmaceutical compositions in tablet form, formulated to provide a controlled and sustained release of a pharmaceutically active ingredient over an extended period of time. The invention also relates to pharmaceutical compositions in the form of buccal tablets or sub-lingual lozenges and to a device for retaining a sustained release or buccal tablet in place in a patient's mouth.

It has been recognised, for more than 10 years, that patients in intensive care units, particularly those who require artifical ventilation, are extremely susceptible to bacterial infection. In many cases, despite good nursing care, patients die from bacterial infection rather than from an original traumatic injury. Gram-negative bacteria are responsible for most of these potentially pathogenic infections. Once a patient has been admitted to hospital, his endogenous aerobic flora are replaced by nosocomial (hospital originating) gram-negative bacteria, such as Pseudomonas, Acinetobacter and, Klebsiella, which may rapidly colonise the oropharynx, stomach and. intenstines. Once the digestive tract has been so colonised, subsequent colonisation and infection of major organ systems may occur.

More than 80% of critically ill patients are colonised by nosocomial gram-negative bacteria within 10 days of admission to hospital (Northey et al. (1974), Surgery, Gynaecology, and Obstetrics 139, 321–5: Sheild, Hammill and Neale (1979), Intensive Care Medicine 5, 171–81 and; Thorpe, Richards and Telfer (1979) Anaesthesia 34, 643–50) and these organisms are responsible for the majority of late infections (Rose & Babcok (1975) American Journal of Epidemiology 101, 495–501 and; Weinstein and Kabins (1981) American Journal of Medicine 70, 449–54). Considerable success has been achieved in reducing the incidence of such infection by the prophylactic administration of non-absorbable antibiotics to selectively decontaminate the digestive tract. The antibiotics are selected to the potentially pathogenic aerobic gram-negative micro-organisms from the digestive tract, leaving the mainly endogenous anaerobic flora substantially unaffected. This work was carried out by C. P. Stoutenbeek and H. K. F. Van Saene and co-workers since 1982 and has been reported in: Journal of Antimicrobial Chemotherapy (1984) 14, supplement B, 203–211; Journal of Antimicrobial Chemotherapy (1987) 19 , 513–520 and; Intensive Care Medicine (1986) 12 , 419–423. The non-absorbable antibiotics were administered through a nasogastric tube, in the form of an extemporaneously prepared suspension of Polymyxin E (15%), Tobramycin (12%) and, amphotericin (73%), and applied to the buccal mucosa in the form of a commercially available paste (ORABASE Registered Trade Mark, available from Squibb) containing 2% polymyxin E, 2% tobramycin and 2% amphotericin B. Both preparations were administered to patients every four hours, with gastric suction being applied for the first hour after administration. To prevent infections of the respiratory tract, systemic antibiotic prophylaxis may also be given to multiple trauma patients.

Although prophylactic and selective decontamination of the digestive tract has proven to be very successful, it is difficult and time consuming in application. These difficulties have prevented the method from becoming more widely used.

According to a first aspect of the present invention there is provided a pharmaceutical tablet or lozenge, comprising a non-absorbable pharmaceutically active agent in combination with a tablet matrix arranged for providing controlled and sustained release of said agent into the mouth and gastro-intestinal tract, from a buccal or sub-lingual location. The term non-absorbable, when used herein to describe a pharmaceutically active agent, defines such an agent that is not absorbed into the blood, or bodily fluids in any substantial quantity from a normal and untraumatised human digestive tract.

Preferably, the tablet matrix is formulated so as to be erodible on exposure to the fluid present within the mouth.

An advantage of a pharmaceutical tablet or lozenge in accordance with the present invention is that when placed in a buccal or sub-lingual location in a patient's mouth, the tablet provides a controlled and sustained dose of the pharmaceutically active agent to the entire digestive tract, from the mouth to the large intestine. Since the pharmaceutically active agent is non-absorbable, any systemic side effects that the agent may have are avoided and the likelihood of creating resistance to the agent is reduced. When the tablet matrix is chosen to be erodible, no residue or empty shell remains in a patient's mouth after the active agent has ken discharged.

Buccal tablets, sub-lingual lozenges and conventional pharmaceutical tablets are all formulated to include pharmaceutically active components. The distinction between a buccal tablet and a conventional pharmaceutical tablet arises from the manner in which a buccal tablet is used. In use, a buccal tablet is placed between the lip and the gum and allowed to dissolve, or otherwise release its pharmaceutically active component. With all hitherto known buccal tablets, this active component is then absorbed through buccal tissues of the mouth. A sub-lingual lozenge is similar, however it is designed to be placed under the tongue to dissolve, or otherwise release its pharmaceutically active component, which, conventionally, is absorbed through the sub-lingual area of the mouth.

Erodible pharmaceutical tablets formulated to provide a sustained and controlled release of a medicament from within the stomach are known and, for example, may be formed by compressing a hydroxypropylmethyl cellulose (available from the Dow Chemical Corporation under the Trade Mark Methocel) in admixture with a pharmaceutically active ingredient and other pharmaceutical excipients. See "Formulating Sustained Released Pharmaceutical Products with Methocel" The Dow Chemical Co., 1982. However, in these tablets the active ingredient is of a type which acts systemically by oral administration into the gastro-intenstinal tract, followed by subsequent absorption into the blood.

Controlled release buccal tablets and sub-lingual lozenges may also be formed from hydroxypropylmethyl cellulose and a suitable medicament. However as suggested above, such tablets and lozenges, conventionally, contain medicaments which are absorbed through the buccal or sub-lingual tissues of the mouth.

Compositions for sustained and controlled release tablets, including buccal tablets and sub-lingual lonzenges, are described in British Patent No. 1583801 and Published British Patent Application Nos. 2061950; 2111386 and 2117239 and European Patent Application No. 0157695, all in the name of Forest Laboratories Incorporated of 150 East 58th Street, New York, N.Y. United States of America.

In a preferred embodiment of the first aspect of the present invention, the tablet matrix includes a water soluble cellulose derivative, which may be a hydroxypropylmethyl cellulose or a mixture of hydroxypropylmethyl celluloses. In a preferred embodiment, the tablet matrix includes an ethyl cellulose and a salt of carboxymethyl cellulose, preferably the sodium salt.

Hydroxypropylmethyl celluloses are commercially available in several different grades. These include METHOCEL E,F,J, and K manufactured by the Dow Chemical Co in the United States, HPM, manufactured by British Celanese, Limited and METALOSE SH manufactured by Shin-Etsu KK in Japan. The various grades available under each of the aforementioned Trade Marks represent differences in methoxy and hydroxypropyl content as well as molecular weight. The designations of the various hydroxypropylmethyl celluloses are based on the viscosities of 1% aqueous solutions at 20° C. The viscosities range form 15 cps to 30,000 cps.

The rate at which an active ingredient is released from a tablet in accordance with the present invention held in a buccal, or sub-lingual location and the total period over which such a tablet remains active maybe determined by altering the total and relative amounts of different grades of hydroxypropylmethyl cellulose in the tablet matrix. Thus, for example, a tablet may be formulated to release its entire dose in a matter of minutes, or to release its dose at an even rate over a period of several hours. Up to eight hours being possible.

In a preferred embodiment, the non-absorbable pharmaceutically active agent is a non-absorbable antibiotic agent, or a mixture of such agents. Preferably, said antibiotic agent or agents is or are selected to have a narrow spectrum of activity and to be active only against selected potentially pathogenic organisms. A tablet or lozenge in accordance with these preferred embodiments may be administered to a patient, in a buccal or sub-lingual location, in order to provide the patient with a sustained prophylactic dose of antibiotics and to selectively decontaminate the patient's digestive tract. Thus the complexities of the previously practiced method of prophylactic and selective decontamination of the digestive tract, including the use of a nasogastric tub extemporaneously prepared antibiotic mixtures and gastric suction, may be replaced by the simple and regular administration of a tablet in accordance with the present invention to the buccal or sub-lingual area of the patient's mouth.

In a further embodiment of the present invention, the non-absorbable antibiotic agent is a non-absorbable aminoglycoside, a non-absorbable polymyxin, a non-absorbable polyene, a non-absorbable substituted imidazole derivative, or a mixture of such agents. Preferably, a tablet in accordance with the present invention includes at least two and preferably three such antibiotic agents. More preferably the antibiotic agents belong to different ones of the above classes.

The non-absorbable aminoglycoside may be a non-absorbable form of tobramycin, framycetin, neomycin, netilmicin, gentamicin, or streptomycin. The non- absorbable polymyxin may be colistin sulphate, or sulphur methylated coilstin. The antifungal polyene may be nystatin or amphotericin B. The non-absorbable substituted imidazole derivative maybe non-absorbable forms of ketoconazole, miconazole or, clotrimazole.

In a further embodiment, the tablet matrix comprises a salivation promotion agent, an inert tablet filler and an inert tablet lubricant. Varying the amount and nature of the fillers and lubricants in a tablet or lozenge, provides a further method of adjusting the rate of release of an active ingredient and the period over which the ingredient is released.

In an alternative embodiment, the non-absorbable agent is selected for treating the digestive tract of immuno compromised patients, such as those with leukaemia or HIV infection or others who have undergone transplant surgery. In a further alternative embodiment the non-absorbable agent is benzylmetronidazole.

Two buccally administered pharmaceutical preparations are currently available in the United Kingdom. The first is sold under the Trade Mark SUSCARD BUCCAL by Pharmax Ltd. of Bourne Road, Bexley, Kent. and includes lactose in its formulation, together with glyceryl trinitrate as the active ingredient. The second preparation is sold under the Trade Mrk BUCCASTEM by Reckitt and Colman Ltd. of Dansom-Lane, Hull, North Humberside, and contains sucrose in its formulation, together with prochloroperazine maleate as the active ingredient.

Since both lactose and sucrose are carigenic it is most likely, in view of their site of administration, that repeated use of buccal tablets or sub-lingual lozenges containing these sugars will cause dental caries. The risk of causing dental caries would be particularly acute with sustained and controlled release buccal tablets or sub-lingual lozenges including sucrose or lactose, because these must reside in a patient's mouth for long periods of time.

According to a second aspect of the present invention there is provided a pharmaceutical tablet or lozenge for administration in a buccal or sub-lingual location, comprising a pharmaceutically active agent in combination with a non-carigenic sugar. Preferred non-carigenic sugars include sorbitol, mannitol and, xylitol. Advantageously, prolonged use of a tablet in accordance with the present invention will not promote the formation of dental caries in a patient's teeth.

Surprisingly, the administration of buccal or sub-lingual tablets that include non-carigenic sugars does not cause the gastro-intestinal disturbances, that normally are associated with the use of such sugars. This is believed to be because such disturbances result from an immediate administration of the sugar in gram quantities; whereas a typical buccal tablet includes about 100 mg of sugar and the sugar from the tablet is released more slowly than with a conventional tablet.

In a preferred embodiment of the second aspect of the invention, a buccal tablet or sub-lingual lozenge in accordance with the present invention comprises less than 200 mg of non-carigenic sugar and preferably less than 100 mg of non-carigenic sugar.

In a further preferred embodiment of the second aspect of the invention, a buccal tablet or sub-lingual lozenge in accordance with the present invention includes a water soluble cellulose derivative, which may be a hydroxypropylmethyl cellulose or a mixture of hydroxypropylmethyl celluloses. In a preferred embodiment, the tablet includes an ethyl cellulose and a salt of carboxymethyl cellulose, preferably the sodium salt.

Further embodiments of the second aspect of the present invention include hydroxypropyl cellulose, tablet lubricants, such as magnesium stearate, stearic acid, sodium fumarate and colloidial silicon dioxide plus other components, such as flavourings and artifical sweetners, such as aspartame.

The pharmaceutically active ingredient in the composition in accordance with the second aspect of the invention may be selected from a wide range of possibilites. It may be systemically absorbable through the buccal mucosa or sub-lingual tissues of the mouth, or be non-absorbable for administration to the entire digestive tract. Examples of active ingredients suitable for use in compositions in accordance with the second aspect of this invention include antacids, anti-inflamatory substances, coronary vasodilators, cerebral vasedilators, peripheral vasodilators, anti-infectives, psychoteoptics, anti-manics, stimulants, anti-histamines, laxatives, decongestants, vitamins, gastro-intestinal sedatives, anti-diarrheal preparations, anti-anginal drugs, antiarrythmics, anti-hypertensive drugs, vasconstrictors, anti-coagulants, anti-thrombotics, analgesics, anti-pyretics, hypnotics, sedatives, anti-emetics, anti-nausiants, anti-convulsants, neuromuscular agents, hyper- and hypoglycaemic agents, thyroid preparations, diuretics, antispasmodics, mineral and nutritional additives, anti-obessity drugs, anabolic agents, anti-asmatics, expectorants, cough surpressants, antibiotics and other anti-microbial agents, topical analgesics and local anaesthetics and, polypeptides.

In a preferred embodiment of the first aspect of the present invention, the tablet or lozenge is formulated in accordance with the second aspect of the invention and the tablet matrix includes a non-carigenic sugar, such as sorbitol, mannitol or, xylitol. Advantageously, the prolonged use of a tablet in accordance with this preferred embodiment of the first aspect of the present invention will not promote the formation of dental caries in a patient's teeth. Furthermore, as set out above, administration of buccal or sub-lingual tablets that include non-carigenic sugars does not cause the gastro-intestinal disturbances, normally associated with the use of such sugars. This is believed to be because such disturbances result from an immediate administration of the sugar in gram quantities; whereas a typical buccal tablet includes less than 100 milligrams of sugar and the sugar from the tablet is released slowly over a significant period of time.

A difficulty, which has been encountered during the past and in connection with buccal tablets, is that such a tablet may become dislodged from between a patient's lip and gum, before all of its active ingredient has been released. The risk of this eventuality is more acute with patients in intensive care units, who are often partially or totally unconscious.

Accordingly and in a third aspect, the present invention provides a tablet retaining device comprising means engageable to a patient and means for accommodating and retaining a pharmaceutical tablet or lozenge, wherein the device is arranged to hold a tablet or lozenge in a location with a patient's mouth, from which an active ingredient, from the tablet or lozenge, is releasable by the action of the patient's saliva or other fluid within the mouth.

Advantageously, a device in accordance with the third aspect of the present invention can be used to accommodate and retain a pharmaceutical tablet, comprising a pharmaceutically active agent in combination with a table matrix arranged to provide controlled and sustained release of said agent, on exposure to a fluid in a patient's mouth. The pharmaceutically active agent can be non-absorbable and the device, therefore, used in a method of treating a patient's mouth and gastro-intestinal tract with such a non-absorbable agent. Preferably, the device is used to hold a tablet or lozenge in accordance with the first aspect of the present invention, for use in any of the treatments in which tablets or lozenges in accordance with the first aspect of the invention may be used. The most preferred of these treatments is that of providing a patient with a sustained prophylactic dose of antibiotics, to selectively decontaminate the patient's digestive tract.

In a preferred embodiment, a device according to the third aspect of the invention is arranged to hold a tablet in a buccal location between a patient's gum and lip. This preferred embodiment can be used in conjunction with a conventional buccal tablet, or in conjunction with a buccal tablet in accordance with the first or second aspects of the present invention.

An advantage of devices in accordance with the third aspect of the present invention is that, when one is used to hold a tablet in the mouth of a partially or totally unconscious patient, there is no risk of that patient inadvertantly swallowing or choking upon the tablet.

In a most preferred embodiment, the means engagable to a patient are arranged to be engaged upon one, or a plurality of teeth. Also, the device may be configured to hold a plurality of appropriately located tablets.

According to a fourth aspect of the present invention there is provided a pharmaceutical tablet or lozenge in accordance with the first aspect of the invention for administration in a buccal or sub-lingual location in a method comprising the prophylactic and selective decontamination of the human or animal digestive tract.

According to a fifth aspect of the present invention there is provided the use of a composition comprising a non-absorbable pharmaceutically active agent, in combination with a tablet matrix arranged to provide controlled and sustained release of said agent into the mouth and gastro-intestinal tract, from a buccal or sub-lingual location, in the manufacture of a medicament for the prophylactic and selective decontamination of the human or animal digestive tract.

Preferred, non-limiting formulations for buccal tablets in accordance with the present invention are given below. The quantities of each constituent are given in terms of milligrams thereof per tablet. Typically, each tablet will weigh in the order of 50–200mg. Formulations 1 to 3 are in accordance with the first aspect of the invention whereas all of the formulations are in accordance with the second aspect of the invention.

| Ingredient | amount/tablet |
| --- | --- |
| Formulation 1 | |
| Colistin sulphate | 2–15 mg |
| Tobramycin sulphate | 2–15 mg |
| Amphotericin B | 5–40 mg |
| Hydroxypropylmethyl cellulose | 5–150 mg |
| Citric acid | 2–20 mg |
| Mannitol | 0–100 mg |
| Magnesium stearate | 2–10 mg |
| Colloidal silicon dioxide | 2–10 mg |
| Formulation 2 | |
| Colistin sulphate | 2–15 mg |

| | -continued | |
|---|---|---|
| Framycetin | 5–20 | mg |
| Nystatin | 5–40 | mg |
| Hydroxypropylmethyl cellulose | 50–150 | mg |
| Citric acid | 2–20 | mg |
| Mannitol | 0–100 | mg |
| Magnesium stearate | 2–10 | mg |
| Colloidal silicon dioxide | 2–10 | mg |
| Formulation 3 | | |
| Colistin sulphate | 2–15 | mg |
| Netilmicin | 2–15 | mg |
| Clotrimazole | 5–40 | mg |
| Hydroxypropyl cellulose | 50–150 | mg |
| Citric acid | 2–20 | mg |
| Xylitol | 0–100 | mg |
| Stearic acid | 2–10 | mg |
| Colloidal silicon dioxide | 2–10 | mg |
| Formulation 4 | | |
| Glyceryl trinitrate | 1–15 | mg |
| Hydroxypropylmethyl cellulose | 5–150 | mg |
| Citric acid | 2–20 | mg |
| Mannitol | 0–100 | mg |
| Magnesium stearate | 2–10 | mg |
| Colloidial silicon dioxide | 2–10 | mg |
| Formulation 5 | | |
| Prochloroperazine maleate | 2–15 | mg |
| Hydroxypropylmethyl cellulose | 50–150 | mg |
| Citric acid | 2–20 | mg |
| Mannitol | 0–100 | mg |
| Magnesium stearate | 2–10 | mg |
| Colloidal silicon dioxide | 2–10 | mg |
| Formulation 6 | | |
| Colistin sulphate | 2–15 | mg |
| Hydroxypropyl cellulose | 50–150 | mg |
| Citric acid | 2–20 | mg |
| Xylitol | 0–100 | mg |
| Stearic acid | 2–10 | mg |
| Colloidal silicon dioxide | 2–10 | mg |

EXAMPLE 1

One thousand 100 mg buccal tablets in accordance with formulation 1 were prepared from the following ingredients:-

| Ingredient | amount/g |
|---|---|
| Colistin sulphate | 5 |
| Tobramycin sulphate | 4 |
| Amphotericin B | 25 |
| Methocel K | 40 |
| Citric acid | 5 |
| Mannitol | 10 |
| Magnesium stearate | 5 |
| Colloidal silicon dioxide | 6 |

The colistin sulphate, tobramycin sulphate, amphotericin B and the methocel K were mixed together and the remaining ingredients were then added to the blend which, thereafter, was mixed for a total of 30 minutes. The resulting mixture was then compressed in a conventional tableting machine into 1,000 cylindrical tablets, each weighing 100 mg. The pressure applied by the punch of the tableting machine was 5 tons per square inch.

EXAMPLE 2

One thousand 150 mg tablets in accordance with formulation 2 were prepared from the following ingredients:

| Ingredients | amount/g |
|---|---|
| Colistin sulphate | 10 |
| Framycetin | 12 |
| Nystatin | 30 |
| Methocel K | 50 |
| Citric acid | 8 |
| Mannitol | 24 |
| Magnesium stearate | 8 |

| Ingredients | amount/g |
|---|---|
| Colloidal silicon dioxide | 8 |

The colistin sulphate, framycetin, nystatin and methocel K were first mixed together and the remaining ingredients were then added thereto. The resulting mixture was blended for a total of 30 minutes and then compressed into 1,000 cylindrical tablets in a conventional tableting machine. The tableting machine puch compressed each tablet at a pressure of 2 tons per square inch.

EXAMPLE 3

One thousand 200 mg tablets in accordance with formulation 3 were prepared from the following ingredients:

| Ingredients | amount/g |
|---|---|
| Colistin sulphate | 5 |
| Netilmicin | 10 |
| Clotrimzole | 20 |
| Methocel K | 140 |
| Citric acid | 8 |
| Xylitol | 12 |
| Stearic acid | 3 |
| Colloidal silicon dioxide | 2 |

The above ingredients were blended together for a total of 45 minutes and, thereafter, compressed into a 1,000 cylindrical tablets of 200 mg in a conventional tableting machine. The tableting machine punch subjected each tablet to a pressure of 7 tons per square inch.

EXAMPLE 4

One thousand 100 mg buccal tablets in accordance with formulation 1 were prepared from the following ingredients:

| Ingredient | amount/g |
|---|---|
| Glyceryl trinitrate | 5 |
| Methocel K | 30 |
| Citric acid | 9 |
| Mannitol | 45 |
| Magnesium stearate | 5 |
| Colloidal silicon dioxide | 6 |

The Glyceryl trinitrate (absorbed in mannitol), and the methocel K were mixed together and the remaining ingredients were then added to the blend which, thereafter, was mixed for a total of 30 minutes. The resulting mixture was then compressed in a conventional tableting machine into 1,000 cylindrical tablets, each weighing 100 mg. The pressure applied by the punch of the tableting machine was 5 tons per square inch.

EXAMPLE 5

One thousand 150 mg tablets in accordance with formulation 2 were prepared from the following ingredients:

| Ingredients | amount/g |
|---|---|
| Prochloroperazine maleate | 10 |
| Methocel K | 70 |
| Citric acid | 15 |
| Mannitol | 39 |

-continued

| Ingredients | amount/g |
| --- | --- |
| Magnesium stearate | 8 |
| Colloidal silicon dioxide | 8 |

The prochloroperazine maleate and the methocel K were first mixed together and the remaining ingredients were then added thereto. The resulting mixture was blended for a total of 30 minutes and then compressed into 1,000 cylindrical tablets in a conventional tableting machine. The tableting machine puch compressed each tablet at a pressure of 5 tons per square inch.

EXAMPLE 6

One thousand 200 mg tablets in accordance with formulation 3 were prepared from the following ingredients:

| Ingredients | amount/g |
| --- | --- |
| Colistin sulphate | 5 |
| Methocel K | 130 |
| Citric acid | 8 |
| Xylitol | 42 |
| Stearic acid | 8 |
| Colloidal silicon dioxide | 7 |

The above ingredients were blended together for a total of 45 minutes and, thereafter, compressed into a 1,000 cylindrical tablets of 200 mg in a conventional tableting machine. The tableting machine punch subjected each tablet to a pressure of 5 tons per square inch.

the above examples, example 1 to 3 are in accordance with the first aspect of the invention, whereas all of the examples are in accordance with the second aspect of the invention.

A tablet retaining device, in accordance with the third aspect of this invention will now be described, by way of example only, with reference to the following drawings:

Figure 1:
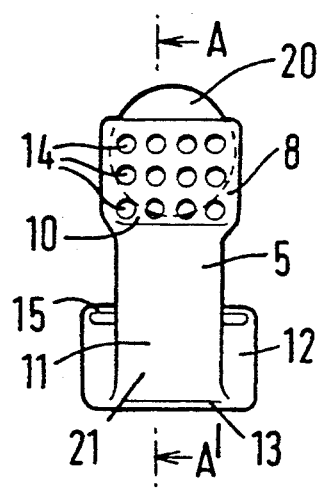
FIG. 1 is a front view of a first such device.
Figure 2:
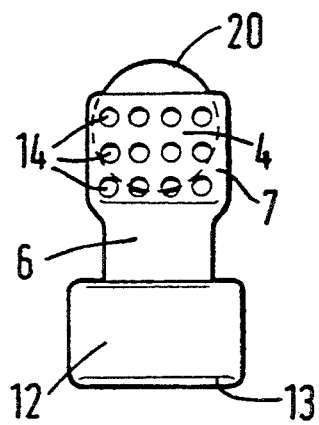
FIG. 2 is a rear view of the device shown in FIG. 1.
Figure 3:
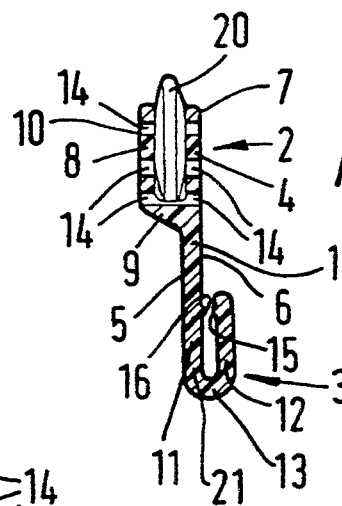
FIG. 3 is a section A-A' in FIG. 1.

The tablet retaining device illustrated in FIG. 1 to 3 is formed from a resilient plastics resin material, such as polystyrene, polycarbonate, or an acrylic plastic resin such as polymethylmethacrylate. The tablet retaining device is integrally formed, preferably by moulding, and includes an elongate leg member 1 which forms a part of and links first and second channel section clip portions 2 and 3.

The elongate leg member 1 has a rectangular cross section, is of substantially uniform thickness along its length and, defines first and second parallel outwardly facing surfaces 5 and 6. A first end portion 7 of the elongate leg member 1, has a greater width than the remainder thereof. The first end portion 7 of the elongate member 1 provides a first rectangular Jaw plate 4 for the first clip portion 2. The first clip portion 2 further comprises a second rectangular Jaw plate 8, spaced apart from the first Jaw plate 4 and parallel thereto. A bridging portion 9, extending from a first margin 10 of the second rectangular Jaw plate 8 to meet the first surface 5 of the elongate leg member 1, where the first end portion 7 broadens out from the remainder thereof, completes the first clip portion 2.

Both the Jaw plates 4 and 8 are substantially square in outline, with facing surfaces of substantially the same area.

The second clip portion 3 comprises a first Jaw plate 11, defined by a second end portion 21 of elongate leg member 1, a second rectangular Jaw plate 12, spaced apart from the first Jaw plate 11 and substantially parallel thereto, and a bridging portion 13. The bridging portion 13 is in the form of an extension to the elongate leg member 1, which curves through approximately 180°, to extend into the second rectangular Jaw plate 12 of the second clip portion 3.

The second Jaw plate 12 of the second clip portion 3 faces the second surface 6 of the elongate leg member 1; whereas the second Jaw plate 8 of the first clip portion 12 faces the first surface 5 of the elongate leg member 1.

The second jaw plate 12 of the second clip portion 3 is of a greater width than the first Jaw plate 11 of the second clip portion 3, the remainder of the elongate leg member 1 and the Jaw plates 4 and 8 of the first clip member 2.

The first and second jaw plates 4 and 8 of the first clip member 2, both define an array of ciruclar cross-section holes 14. The holes 14 defined by the first Jaw plate 4 are in register with corresponding holes 14 defined by the second Jaw plate 8.

A first ridge 15 is defined along the edge portion of the second Jaw plate 12 of the second clip member 3, remote from the bridging portion 13, and faces the second surface 6 of the elongate leg member 1. A second similar ridge 16 extends across the second surface 6 of the elongate member 1, facing the first ridge 15.

Figure 4:
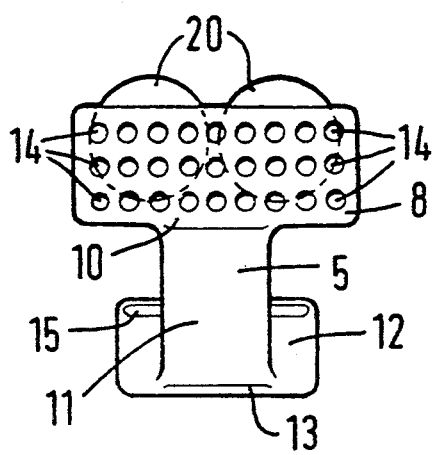
FIG. 4 is a front view of a second device in accordance with the present invention.

The same reference numerals as used above to identify parts of the device shown in FIGS. 1 to 3, are used to identify corresponding parts of the device shown in FIG. 4. The difference between the two devices is that the Jaw plates 4 and 8 of the first clip portion 2, of the device shown in FIG. 4, are of considerably greater width than the remainder of said device and the entire device shown in FIGS. 1 to 3.

The Jaw plates 4 and 8 of the first clip portion 2 in the device shown in FIGS. 1 to 3 are dimensioned and spaced apart, so as to accommodate a tablet 20, in the manner shown in FIGS. 1 to 3. The spacing between the Jaw plates 4 and 8 is chosen so that the tablet 20 is resiliently gripped therebetween. Likewise, the Jaw plates 4 and 8 of the first clip portion 2 in the device shown in FIG. 4, are dimensioned to accommodate two tablets 20 in a side-by-side relationship, as shown in FIG. 4.

To use the device illustrated in FIGS. 1 to 3, a tablet 20 is pushed between the Jaw plates 4 and 8 of the first clip portion 2, until it is located as shown in FIGS. 1 to 3 and tightly gripped between the Jaw plates 4 and 8. The loaded device is then inserted into a patient's mouth 23 and the second clip portion 3 is engaged on a tooth 24 (see FIGS. 5 and 6). The tooth is resiliently gripped between the first and second Jaw plates 11 and 12 of the second clip portion 3, in such a way that the device cannot be accidentally dislodged. The device is installed in the orientation shown in FIG. 6, that is with the first clip portion 2, holding the tablet 20 immediately adjacent to the buccal mucosa 25 and between the latter and the patient's top lip 26 (when the top lip is in the normal relaxed position).

Fluids such as saliva, within the mouth can gain access to the tablet 20 both through the holes 14 and through the gap between the jaw plates 4 and 8 of the first clip portion 2. The holes 14, in the first Jaw plate 4, allow matter disolved from the tablet to pass directly into contact with the buccal mucosa 25.

Figure 5:
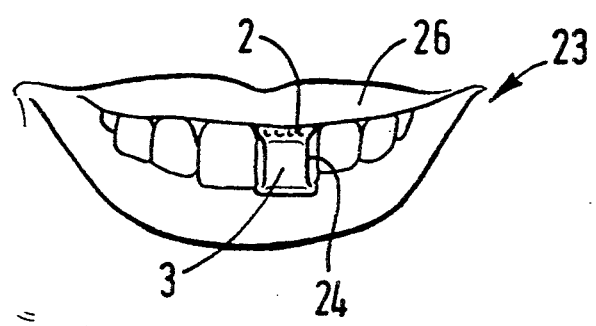
FIG. 5 shows a patient's mouth with a device, as shown in FIG. 1, engaged therein.
Figure 6:
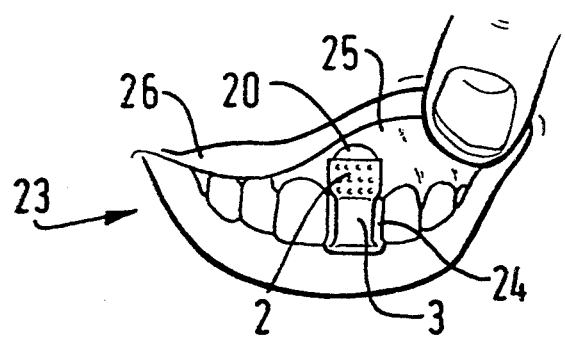
FIG. 6 is a view of the same patient's mouth as shown in FIG. 5, but with the top lip raised so that the tablet retaining device is fully visible.

The illustrated devices can be used in conjunction with any form of tablet which it is desired to hold in the mouth while its active ingredient is leached therefrom. Thus, these devices may be employed to hold conventional buccal tablets, which include active ingredients to be absorbed through the buccal mucosa, sustained release conventional buccal tablets, sustained release tablets containing non-absorbable active ingredients, such as those in accordance with the first aspect of the present invention, and other sustained release tablets whose active ingredients may be absorbed throughout the digestive tract. Most preferably, the device is employed together with tablets in accordance with the first or second aspects of the present invention, especially those formulated in accordance with the above formulations and examples. In this regard, a tablet produced in accordance with one of examples 1 to 6 should be placed in a device as shown in FIGS. 1 to 3 and the device then should be installed in a patient's mouth as shown in FIGS. 5 and 6. The device and tablet should be left in place until the tablet has completely dissolved and, if necessary, removed, reloaded with a fresh tablet and reinstalled in the patient's mouth. The time taken for a given tablet to dissolve and release its phamaceutically active component(s) is dependent upon the type and relative quantity of the Methocel (or the like) which is used, and can be determined by carrying out appropriate trials.

Most preferably, a device as shown in FIGS. 1 to 3 is loaded with a tablet made in accordance with one of examples 1 to 3. Such a loaded device can then be installed in a patient's mouth as aforesaid, to selectively decontaminate his mouth and digestive tract.

As suggested above, the rate at which any given tablet dissolves and releases antibiotic can be determined experimentally. Tablets used for selective decontamination treatment are selected to provide the dose Judged appropriate for a particualr patient, over an appropriate period. Both the daily dose and the period over which it should be provided depend upon a particualr patients dispositon. Thus, for example, a suitable daily dose may be provided by a tablet which dissolves completely within one hour, or at the other extreme may be provided by three, successively administered, tablets that each take eight hours to dissolve.

If the patient's salivary flow is reduced, and during the routine maintenance of oral hygiene, the tablet and device may be sprayed with oral cleansing fluid or an artificial salivary agent to facilitate the dissolution of the tablet.

I claim:

1. A pharmaceutical tablet or lozenge, comprising at least two non-absorbable antibiotic agents, in combination with a tablet matrix for providing controlled and sustained release of said agents, wherein the tablet or lozenge is arranged for providing controlled and sustained release of a prophylactic dose of said antibiotic agents, into the mouth and gastrointestinal tract, from a buccal or sub-lingual location for selectively decontaminating a human or animal digestive tract.

2. A pharmaceutical tablet or lozenge as claimed in claim 1, wherein the non-absorbable antibiotic agents are selected from the group consisting of non-absorbable aminoglycosides, non-absorbable polymyxins, non-absorbable antifungal polyenes and non-absorbable substituted imidazoles selected from non-absorbable forms consisting of ketoconazole, miconazole and clotrimazole.

3. A pharmaceutical tablet or lozenge as claimed in claim 1, wherein the tablet matrix is formulated so as to be erodible on exposure to fluid present within the mouth.

4. A pharmaceutical tablet or lozenge as claimed in claim 3, wherein the tablet matrix includes a water soluble cellulose.

5. A pharmaceutical tablet or lozenge as claimed in claim 3, wherein the tablet matrix includes an ethyl cellulose and a salt of carboxymethyl cellulose.

6. A pharmaceutical tablet or lozenge as claimed in claim 5, wherein the antibiotic agents are selected to have a narrow spectrum of activity and to be active only against selected potentially pathogenic organisms.

7. A method of treating the human or animal body comprising administering a tablet as claimed in claims 1, in a buccal location, between a patient's gum and lip.

8. A tablet or lozenge as claimed in claim 1 wherein the tablet is a buccal tablet.

9. A pharmaceutical tablet or lozenge as claimed in claim 4, wherein the water soluble cellulose derivative comprises at least one hydroxypropylmethyl cellulose.

10. A pharmaceutical tablet or lozenge as claimed in claim 5, wherein the salt of carboxymethyl cellulose is sodium carboxymethyl cellulose.

11. A pharmaceutical tablet or lozenge as claimed in claim 2, containing three of the antibiotic agents.

12. A pharmaceutical tablet or lozenge as claimed in claim 11, wherein each of the three antibiotic agents belongs to a different member of the group.

13. A pharmaceutical tablet or lozenge as claimed in claim 2, wherein each of the at least two antibiotic agents belongs to a different member of the group.

14. A pharmaceutical tablet or lozenge as claimed in claim 1, wherein the tablet or lozenge comprises less than 100 mg of non-cariogenic sugar.

15. A pharmaceutical tablet or lozenge as claimed in claim 4, wherein the water soluble cellulose derivative is selected from the group consisting of hydroxypropylmethyl cellulose, a mixture of hydroxypropylmethyl celluloses, an ethyl cellulose and a salt of carboxymethyl cellulose.

16. A pharmaceutical tablet or lozenge as claimed in claim 14, wherein the non-cariogenic sugar comprises at least one member selected from the group consisting of sorbitol, mannitol and xylitol.

17. A pharmaceutical tablet or lozenge as claimed in claim 2, wherein said tablet or lozenge includes three antibiotic agents.

18. A pharmaceutical tablet or lozenge as claimed in claim 2, wherein the non-absorbable aminoglycosides are selected from non-absorbable forms from the group consisting of tobramycin, framycetin, neomycin, netilmicin, gentamicin, and streptomycin; the non-absorbable polymyxins are selected from the group consisting of colistin sulphate and sulphur methylate colistin; and the antifungal polyenes are selected from the group consisting of nystatin and amphotericin B.

19. A pharmaceutical tablet or lozenge as claimed in claim 1, wherein the tablet matrix comprises a salivation promotion agent, an inert tablet filler and an inert tablet lubricant.

20. A pharmaceutical tablet or lozenge as claimed in claim 1, wherein the antibiotic agents are selected for treating the digestive tract of immuno-compromised patients with leukaemia or HIV infection, or others who have undergone transplant surgery.

21. A pharmaceutical tablet or lozenge as claimed in claim 1, wherein one of the antibiotic agents is benzylmetronidazole.

22. A pharmaceutical tablet or lozenge, comprising at least two non-absorbable antibiotic agents, in combination with a tablet matrix for providing controlled and sustained release of said agents, wherein the antibiotic agents are selected from the group consisting of non-absorbable aminoglycosides, non-absorbable polymyxins, non-absorbable antifungal polyenes and non-absorbable substituted imidazoles, selected from non-absorbable forms consisting of ketoconazole, miconazole and clotrimazole and the tablet or lozenge is arranged for providing controlled release of said antibiotic agents into the mouth and gastrointestinal tract, from a buccal or sub-lingual location.

23. A method of selectively decontaminating a human or animal digestive tract comprising administering a tablet as claimed in claim 22, in a buccal location between a patient's gum and lip.

24. A pharmaceutical tablet or lozenge as claimed in claim 22, for administration in a buccal or sub-lingual location in a method comprising the prophylactic and selective decontamination of the human or animal digestive tract.

25. A pharmaceutical tablet or lozenge as claimed in claim 22, wherein the non-absorbable aminoglycosides are selected from non-absorbable forms from the group consisting of tobramycin, framycetin, neomycin, netilmicin, gentamicin, and streptomycin; the non-absorbable polymyxins are selected from the group consisting of colistin sulphate and sulphur methylate colistin; and the antifungal polyenes are selected from the group consisting of nystatin and amphotericin B.

26. A pharmaceutical tablet or lozenge as claimed in claim 22, wherein the tablet matrix comprises a salivation promotion agent, an inert tablet filler and an inert tablet lubricant.

27. A pharmaceutical tablet or lozenge as claimed in claim 24 arranged for administration in a tablet retaining device comprising means engageable to a patient and means for accommodating and retaining a pharmaceutical tablet or lozenge, wherein the device is arranged to hold a tablet or lozenge in a location within a patient's mouth from which an active ingredient, from the tablet or lozenge, is releasable by the action of the patient's saliva or other fluid within the mouth.

28. A pharmaceutical tablet or lozenge comprising a non-absorbable pharmaceutically active agent comprising at least one member selected from the group consisting of an aminoglycoside, a polymyxin, a polyene, an imidazole and benzylmetronidazole, in combination with a tablet matrix comprising at least one member selected from the group consisting of a salivation promotion agent, an inert tablet filler, and an inert tablet lubricant arranged for providing controlled and sustained release of said agent into the mouth and gastrointestinal tract, from a buccal or sub-lingual location.

29. A method of selectively decontaminating a human or animal digestive tract comprising administering a tablet comprising a non-absorbable pharmaceutically active agent, in combination with a tablet matrix arranged for providing controlled and sustained release of said agent into the mouth from a buccal location between a patient's gum and lip wherein the non-absorbable pharmaceutically active agent comprises at least one non-absorbable antibiotic agent wherein said tablet is retained in a device comprising means engageable to a patient and means for accommodating and retaining a pharmaceutical tablet or lozenge, wherein the device is arranged to hold a tablet or lozenge in a location within a patient's mouth from which an active ingredient, from the tablet or lozenge, is releasable by the action of the patient's saliva or other fluid within the mouth.

30. A method of selectively decontaminating a human or animal digestive tract comprising administering a tablet comprising a non-absorbable pharmaceutically active agent, in combination with a tablet matrix arranged for providing controlled and sustained release of said agent into the mouth from a buccal location between a patient's gum and lip wherein the non-absorbable pharmaceutically active agent comprises at least one non-absorbable antibiotic agent.

31. A tablet or lozenge as claimed in claim 22, wherein the tablet is a buccal tablet.

* * * * *